(12) United States Patent
Leontopoulou et al.

(10) Patent No.: US 6,382,978 B1
(45) Date of Patent: May 7, 2002

(54) GUM HEALTH GUIDE

(75) Inventors: Sophie Leontopoulou; Ivor Martindale, both of Bebington (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/589,014

(22) Filed: Jun. 7, 2000

(30) Foreign Application Priority Data

Jun. 8, 1999 (EP) ............................................. 99304439

(51) Int. Cl.7 .................................................. A61C 5/00
(52) U.S. Cl. .......................................... 433/215; 433/26
(58) Field of Search ................... 433/26, 215; 434/262, 434/263, 366

(56) References Cited

U.S. PATENT DOCUMENTS

| | | | |
|---|---|---|---|
| 3,571,947 A | * | 3/1971 | Maddison et al. ...... 434/262 X |
| 4,877,580 A | | 10/1989 | Aronowitz et al. |
| 5,009,507 A | | 4/1991 | Katz |
| 5,727,949 A | * | 3/1998 | Bar-Or et al. .......... 434/262 X |

FOREIGN PATENT DOCUMENTS

| | | |
|---|---|---|
| EP | 0 056 877 | 8/1982 |
| EP | 0 779 508 | 4/1994 |
| WO | 92/14402 | 9/1992 |

OTHER PUBLICATIONS

International Search Report.
European Search Report.

* cited by examiner

Primary Examiner—Nicholas D. Lucchesi
(74) Attorney, Agent, or Firm—Milton L. Honig

(57) ABSTRACT

A guide (1) for assessing the general health of the oral cavity comprises at least one indicator (8), characterised in that the indicator (8) is capable of being compared with gums to provide an indication of the general state of the health of the gums.

9 Claims, 5 Drawing Sheets

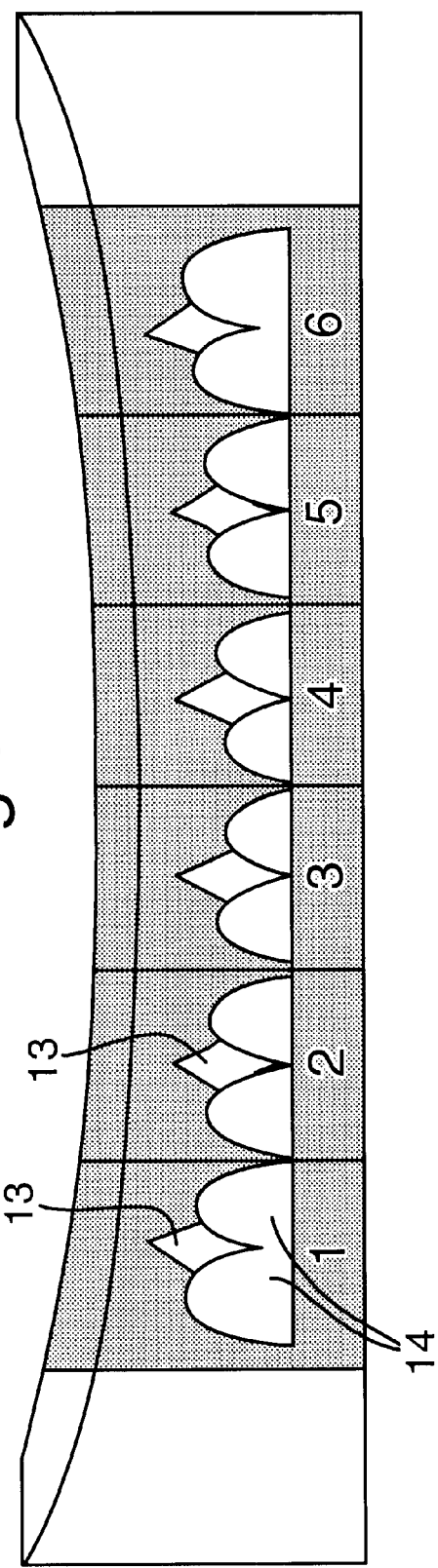

GUM HEALTH GUIDE

BACKGROUND OF THE INVENTION

1. Field of the Invention

The present invention relates to a guide for assessing the general state of health of the gums. It also relates to the use of a guide and to a kit of parts comprising a guide and a oral composition.

2. The Related Art

Dentifrices which provide a whitening benefit are well known in the art. Typically, such dentifrices comprise abrasive agents or bleaches which provide this whitening effect. The concept of a whitening dentifrice is an attractive one for consumers who have stained teeth and wish to improve the cosmetic appearance of the teeth.

Unfortunately, it is difficult to assess the whitening capability of such dentifrices and, to this end, some whitening dentifrices are sold with a shade guide which allows the user to assess the whitening effect of the dentifrice.

Dentifrices which provide a gum health benefit are also known in the prior art. For example, our co-pending application WO 99/59536 describes a dentifrice which is capable of improving the permeability barrier of the gums, thereby reducing the risk of bacterial infection.

Unfortunately, the general state of the gums is not readily apparent to the consumer. Bleeding of the gums can be a signal to the consumer that the gums are not in the proper condition, but while bleeding occurs often during brushing, with or without the accompaniment of pain it does not always occur when the gums are not in prime condition, so the consumer does not get a signal of the gums not being in prime condition.

Accordingly, it is an object of this invention to provide a means for assessing the general state of health of the gums. In particular, there is provided a means for assessing the improvement of the general state of health of the gums through the use of a dentifrice which provides a gum health benefit.

SUMMARY OF THE INVENTION

Accordingly, the present invention provides a guide for assessing the general health of the oral cavity comprising at least one indicator, characterised in that the indicator is capable, on comparison with gums, to provide an indication of the general state of the health of the gums.

Preferably, the indicator comprises a colour indication which corresponds to a particular state of health of the gums. For example, the indicator may be coloured pale pink to correspond with the colour of gums in a good state of health; dark red to correspond with the colour of gums in a poor state of health; or somewhere in the middle corresponding with the colour of gums in an intermediate state.

The indicator may also comprise a means for enabling simultaneous in situ comparison between the gums and the indicator. For example, it may comprise one or more regions of coloured indication and one or more apertures through which the gums may be visualised and compared to the colour indication. The means may equally be the edge of the indicator.

In a preferred embodiment the guide comprises more than one indicator so that change in the state of health of the gums may be monitored. For example, the guide may comprise six indicators differently shaded to correspond to six varying degrees of good/bad gum health. The various indicators may be provided with a tenet, indicating the degree of the gum health.

A guide comprising a plurality of such indicators may present the indicators in a graduated form, i.e. they may be presented in an order from pale pink, through to dark red, corresponding to good to poor health of the gums.

It is envisaged that several guides may be available which provide differently shaded indicators to represent the differing shades of healthy gums, which exist between different racial groups. However, it is understood that the indication of gum disease is the same in such groups, i.e. an increase in redness.

A guide comprising a plurality of indicators may consist of a single entity with several indicators graphically displayed on a same surface. It may equally comprise a plurality of separate indicators, which may or may not be linked in a graduated or ungraduated fashion. For example, they may be linked through a ring or a pivot.

The guide according to the invention may also comprise a handle allowing the user to self-assess the state of gum health more easily.

Another feature of the present invention is a guide comprising a lip retractor. Such a retractor enables the user to hold back the gums and compare the indicators with the gums. A preferred retractor will comprise part of the unitary structure of the guide.

In a more preferred embodiment the lip retractor is a temporary feature capable of being formed and removed through the use of the guide. For example, the guide has a lip retractor region and a guide region separated by a fold. Both are maintained in the nominal plane of the guide. When the guide is in use it is bent slightly and the lip retractor emerges from the nominal plane of the guide and becomes capable of holding the lips back from the gums and enabling use of the device.

Preferably the lip retractor provides strong enough support to hold back the lip to enable use of the guide. While the lip retractor may be separated from the remainder of the guide by way of a straight line fold it is preferred that the fold be curved thereby providing a greater support to the lip.

In a further embodiment the guide also comprises a dentition graphic. This provides a more accurate comparison between the gums and the indicators since it is the region of the gums between the teeth which are most susceptible to disease and the presence of white teeth can easily affect the judgment of the user. Accordingly, the graphic may comprise a display of teeth with apertures provided at the interdental regions to allow the user to assess the health of the gums between the teeth.

In an alternative aspect, the invention provides for the use of a guide according to the invention for the assessment of gum health.

The present invention also provides a kit of parts comprising a guide according to the invention and an oral care composition. Such a kit of parts may comprise the guide and the oral composition packaging attached to one another. Such attachment may be permanent, i.e. the guide is part of the external dentifrice packaging (tube or external packaging) or frangible. The oral composition may be any such composition commonly available commercially, e.g. toothpaste, chewing gum, mouthwash, etc.

BRIEF DESCRIPTION OF THE DRAWING

FIG. 7b is an elevational view of the same guide as FIG. 7a.

FIG. 8 is a fifth embodiment of the guide according to the invention.

DETAILED DESCRIPTION

The invention will now be described by reference to the following non-limiting figures.

Figure 1:
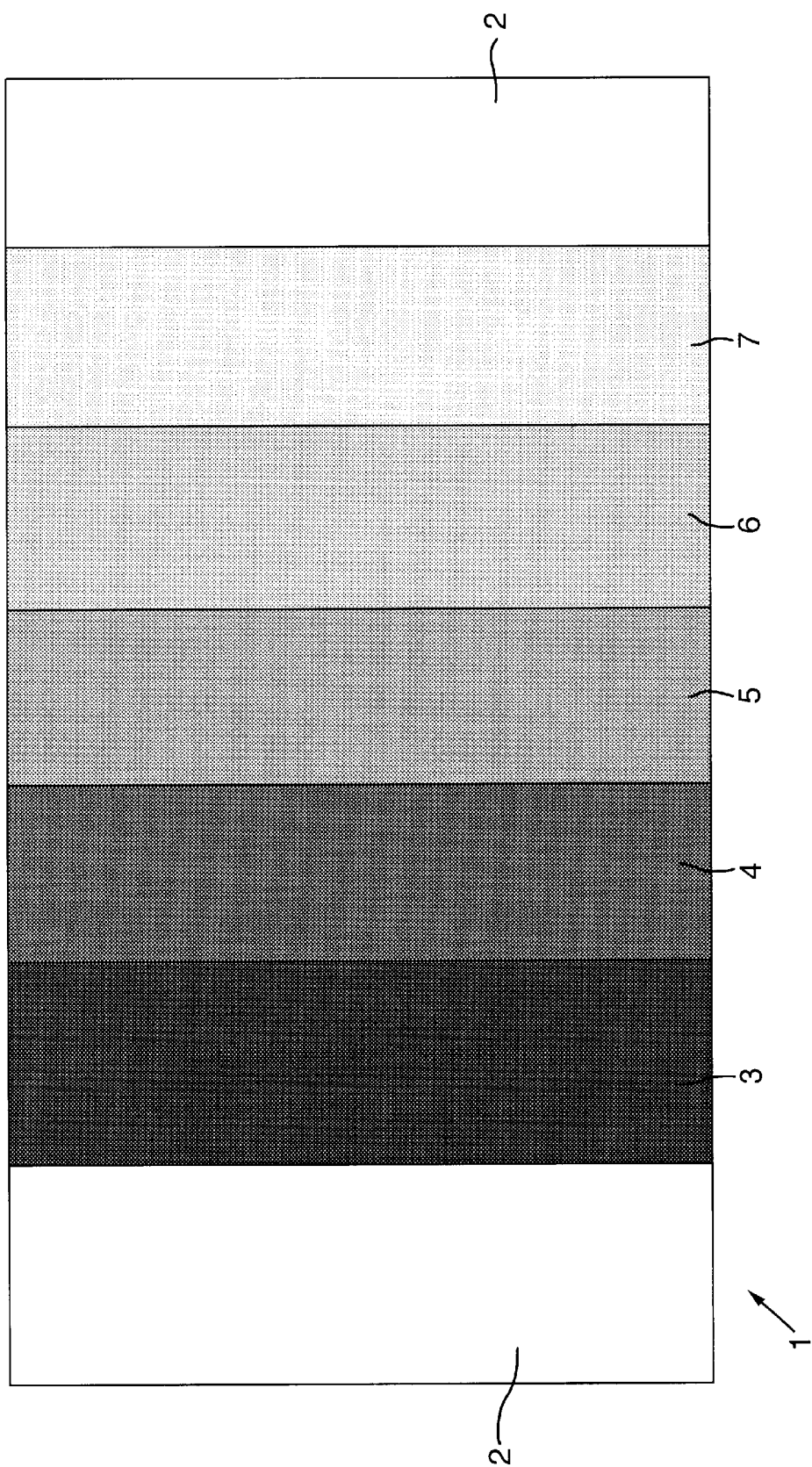
FIG. 1 is a plan view of a guide according to the invention.

FIG. 1 is a plan view of a guide according to the invention. The guide itself (1) is flat and comprises two handles (2) and a series of indicators (3 to 7) each comprising a colour indication which can be compared with the colour of the gums. In this way the user can self assess the general state of health of the gums by comparing their colour with that of an indicator.

The figure also comprises a plurality of indicators arranged in a graduated fashion: from dark red (3) to pale pink (7).

Figure 2:
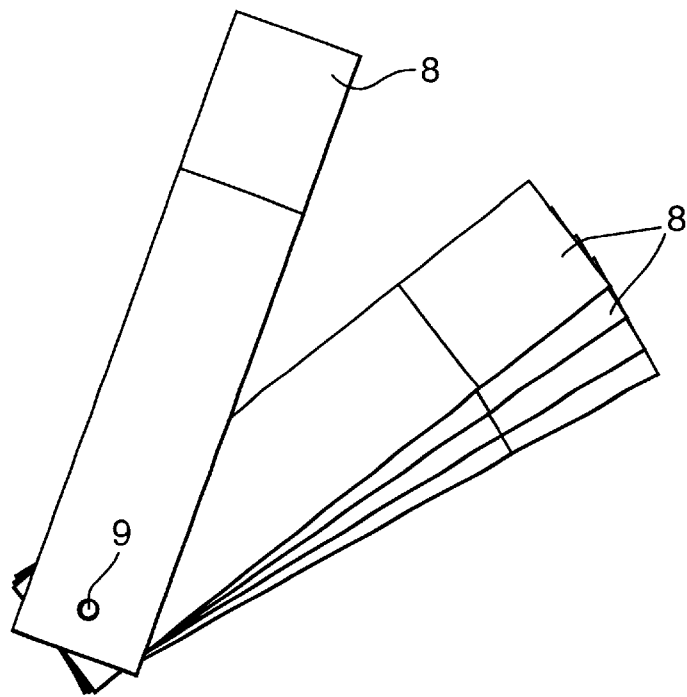
FIG. 2 is a plan view of a second embodiment of the guide.

FIG. 2 is a plan view of a guide according to the invention. This guide is not planar and comprises a plurality of indicators (8) attached through a common point (9). Such attachment may be a pin or just a ring and would allow any indicator to be moved in a circular motion, around the common point (9), with respect to the others.

Figure 3:
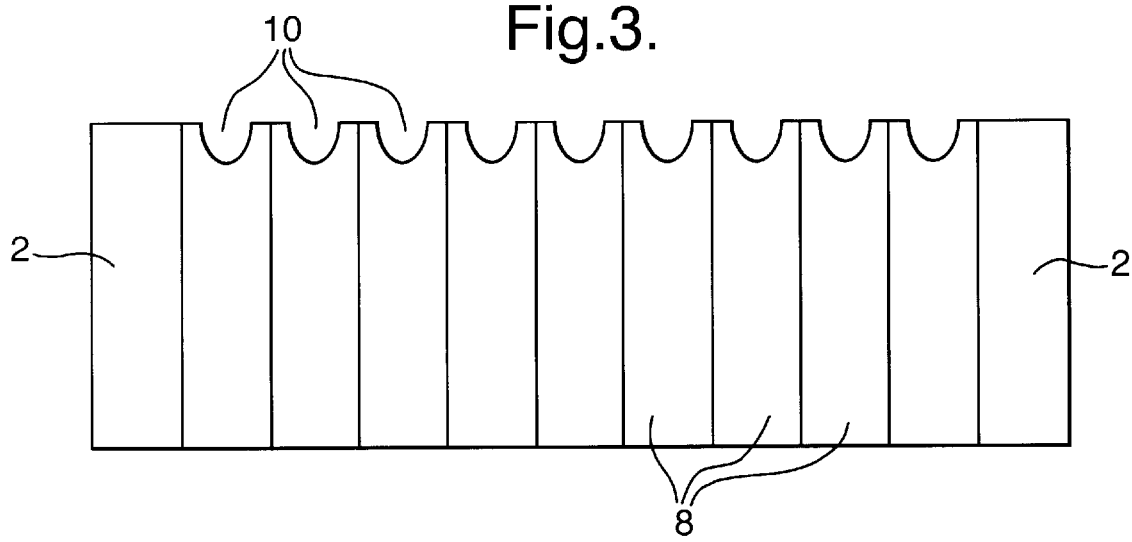
FIG. 3 is a plan view of a third embodiment of the guide.

FIG. 3 is a plan view of a guide according to the invention. The indicators in this case comprise a means for more easily comparing the colour of the gums to that of the indicators. In this case, the means is a notch (10) in the indicator (8).

Figure 4:
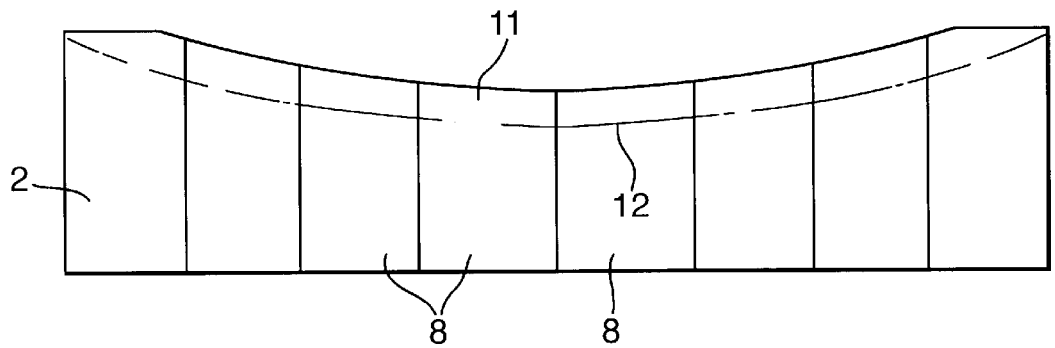
FIG. 4 is a plan view of a fourth embodiment of the guide.

FIG. 4 is a plan view of a guide according to the invention comprising a lip retractor (11). The lip retractor (11) is separated from the remainder of the guide by way of a fold (12).

Figure 5:
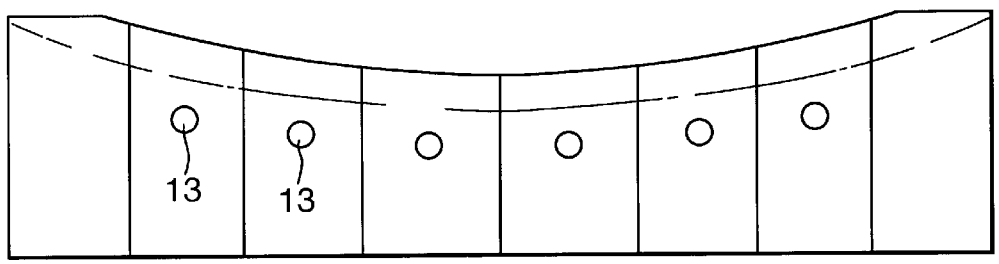
FIG. 5 is a plan view of an embodiment similar to FIG. 4 with modification.

FIG. 5 is a plan view of a guide according to the invention comprising a lip retractor, which also comprises means for simultaneously comparing the colour of the gums with the colour of the indicators by way of apertures (13).

Figure 6:
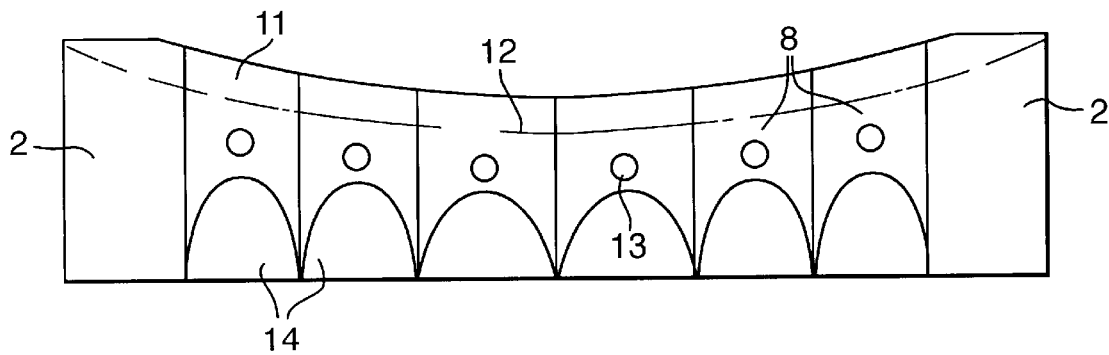
FIG. 6 is a plan view of a guide similar to FIG. 4 and 5 with further modifications.

FIG. 6 is a plan view of a guide according to the invention. It comprises two handles (2); a lip retractor (11), which is separated from the remainder of the guide by a curved fold (12); a plurality of indicators (8) each of which has an aperture (13); and a dentition graphic (14) enabling more accurate comparison with the interdental periodontal tissue.

Figure 7A:
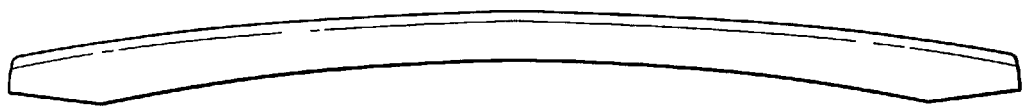
FIG. 7a is a top view of the guide according to FIG. 5 and 6.
Figure 7B:
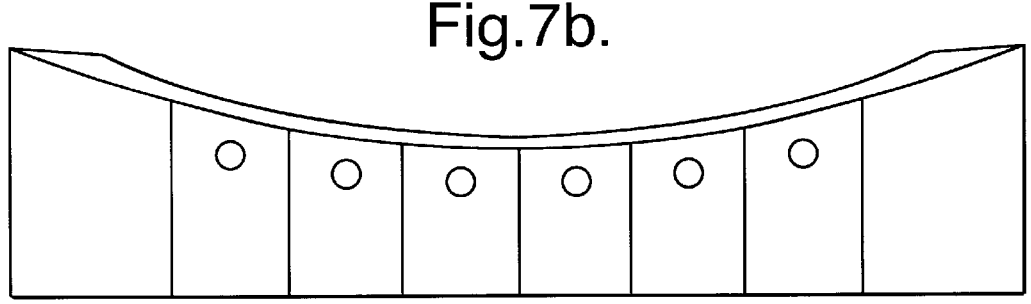
Figure 7C:
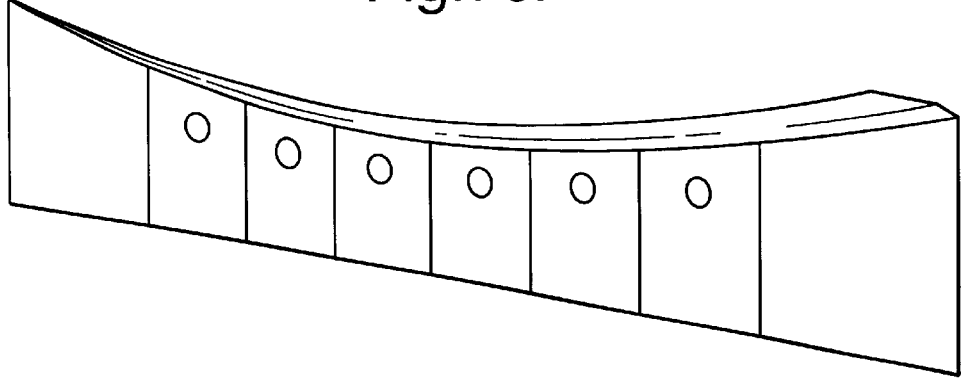
FIG. 7c is a perspective view of the guides shown in FIG. 7a and 7b.

FIG. 7 illustrates the use of the guide shown in FIG. 6. FIG. 7a) is a plan view of a folded guide looking down on the lip retractor. It can be seen that folding the lip retractor creates a curve in the remainder of the guide. FIG. 7b) is an elevational view of the same guide showing the lip retractor folded forwards. FIG. 7c) is a perspective view of the same guide.

FIG. 8 is a further example of a guide according to the invention. Shown is the dentition graphic (14) with apertures (13) spaced between representations of individual teeth to facilitate the comparison of the colour of the interdental regions of the gums with the colour of the guide.

A guide according to the present invention is visualised to have a limited life span although this is not an essential feature. For example, a low-cost guide may be made from paper, which may optionally be laminated, or similar soft material and be made to be used once or twice a month. Naturally, by presenting such a device to the oral cavity there is the risk of bacterial contamination. An alternative design may comprise a more durable material, such as plastic and may optionally comprise an antibacterial substance.

It is envisaged that a guide according to the invention may be manufactured by conventional methods.

What is claimed is:

1. A method for assessing general health of gums in an oral cavity comprising providing an assessment guide having a plurality of indicators and comparing the plurality of indicators against gums in the oral cavity to ascertain the general state of health of the gums, the guide comprising a means for comparing the gums and the indicator simultaneously in situ.

2. The method according to claim 1 wherein the plurality of indicators comprises a color indication corresponding to a particular state of health of the gums.

3. The method according to claim 1, wherein the guide comprises an aperture for comparing the gums and the indicator simultaneously in situ.

4. The method according to claim 1 wherein the guide comprises a plurality of differently shaded indicators.

5. The method according to claim 1 wherein the guide comprises a plurality of different shaded indicators which shading is graduated.

6. The method according to claim 1 wherein the guide comprises a handle.

7. The method according to claim 1 wherein the guide comprises a dentition graphic.

8. A kit comprising a package containing an oral care composition and a guide for assessing general health of gums in an oral cavity, the guide comprising a plurality of indicators for comparison against the gums in the oral cavity to ascertain the general state of health of the gums.

9. A method for assessing general health of gums in an oral cavity comprising providing an assessment guide having a plurality of indicators and comparing the plurality of indicators against gums in the oral cavity to ascertain the general state of health of the gums, the guide comprising a lip retractor.

* * * * *